(12) United States Patent
Decker et al.

(10) Patent No.: US 11,305,107 B2
(45) Date of Patent: Apr. 19, 2022

(54) EMS GARMENT

(71) Applicant: MIHA BODYTEC GMBH, Gersthofen (DE)

(72) Inventors: Jürgen Decker, Aichach (DE); Arno Körner, Herrsching (DE)

(73) Assignee: MIHA BODYTEC GMBH, Gersthofen (DE)

( * ) Notice: Subject to any disclaimer, the term of this patent is extended or adjusted under 35 U.S.C. 154(b) by 64 days.

(21) Appl. No.: 16/574,737

(22) Filed: Sep. 18, 2019

(65) Prior Publication Data

US 2020/0061366 A1 Feb. 27, 2020

Related U.S. Application Data

(63) Continuation of application No. PCT/EP2018/025062, filed on Mar. 14, 2018.

(30) Foreign Application Priority Data

Apr. 5, 2017 (DE) .......................... 102017003321.8

(51) Int. Cl.
*A61N 1/04* (2006.01)
*A61N 1/32* (2006.01)
(Continued)

(52) U.S. Cl.
CPC ............ *A61N 1/0484* (2013.01); *A41D 1/04* (2013.01); *A61N 1/0452* (2013.01); *A61N 1/321* (2013.01); *A61N 1/36014* (2013.01)

(58) Field of Classification Search
CPC .... A61N 1/0484; A61N 1/0452; A61N 1/321; A61N 1/36014; A61N 1/0492; A41D 1/04; A41D 1/002
See application file for complete search history.

(56) References Cited

U.S. PATENT DOCUMENTS 6,341,237 B1 * 1/2002 Hurtado ............. A61N 1/36014
607/148
6,570,056 B1 * 5/2003 Tanzer .............. A61F 13/49009
604/368
(Continued)

FOREIGN PATENT DOCUMENTS

| CN | 102048255 A * 5/2011 |
| DE | 202110506682 U1 9/2011 |
| DE | 202013104554 U1 12/2013 |

OTHER PUBLICATIONS

International Search Report cited in German Appln. No. 102017003321.8 filed Apr. 5, 2017.
(Continued)

*Primary Examiner* — Carl H Layno
*Assistant Examiner* — Anh-Khoa N Dinh
(74) *Attorney, Agent, or Firm* — Bacon & Thomas, PLLC

(57) ABSTRACT

An EMS garment for enclosing a body part of a trainee during an EMS training session includes textile area sections and EMS electrodes for transmitting EMS stimuli from a connected EMS stimulation generating unit to the body part, which EMS electrodes are each connected to one of the textile area sections and are each formed as a pad or a textile structure section having an electrically conductive layer so as to flexibly snuggle to the body part. The textile area sections facing the front side and the rear side are connected along a height direction by stretch sections facing both flanks of the body part, each of which consists of a rubber-elastic, elastomeric solid material.

12 Claims, 3 Drawing Sheets

(51) Int. Cl.
*A61N 1/36* (2006.01)
*A61D 1/04* (2006.01)
*A41D 1/04* (2006.01)

(56) References Cited

U.S. PATENT DOCUMENTS

| | | |
|---|---|---|
| 6,760,629 B2 * | 7/2004 | Minogue ................ A61N 1/321 |
| | | 607/149 |
| 7,072,721 B1 | 7/2006 | Trent |
| 2006/0201178 A1 * | 9/2006 | Smolko ..................... F25D 7/00 |
| | | 62/259.3 |
| 2016/0303363 A1 * | 10/2016 | Girouard .............. A61N 1/0456 |
| 2016/0335632 A1 * | 11/2016 | Proud ...................... A61B 5/08 |

OTHER PUBLICATIONS

International Preliminary Report on Patentabillity in corresponding PCT Appln. No. PCT/EP2018/025062.

* cited by examiner

EMS GARMENT

BACKGROUND OF THE INVENTION

1. Field of the Invention

The invention concerns an EMS garment, as it is required for conducting EMS training.

2. Description of Related Art

EMS stands for electro-muscle stimulation, also known as electro-myo-stimulation. Therein, in fitness studios or at personal trainers, muscles in the living body are stimulated electrically to strengthen the muscles for muscle building purposes. Therein, large-area, usually textile electrodes, in the following referred to as EMS electrodes, are used. In contrast to medical applications such as defibrillators, for example, it is not necessary to transmit extremely high voltages, but rather to ensure good electrode placement on the body, hygiene for changing users and comfort when putting on EMS garments equipped with EMS electrodes. The voltage surges sent to the electrodes for electro-muscle stimulation by corresponding stimulation generating units have an amplitude that is 10 times lower than that used in defibrillators or similar devices. The peak values of the output voltage in the EMS field are generally 70 to 160 volts with a current strength of 10 to 20 mA.

Thus, clocked pulse currents are generated in the EMS stimulation generation unit and conducted through power lines to EMS electrodes and via the EMS electrodes through the body. Usually, the EMS electrodes are connected in pairs so that at one point in time a first EMS electrode is impulsed with the current and a second EMS electrode not, in order to allow the current conducted through the body to flow off at this point in time. When the pulse is changed, the second EMS electrode is impulsed with current and the first EMS electrode is not. The current flow is even more complex with garment with several pairs of EMS electrodes, e.g. chest, abdomen, back, upper arms, thighs, etc.

The EMS electrodes are connected to the EMS stimulation generation unit, i.e. a control unit that operates, for example, in a frequency range from 2 to 150 Hz with a pulse width of 50 to 400 microseconds and a pulse pause of 0 to 10 seconds. The maximum peak value of the electrical output voltage is, for example, 70 to 160 V with a current strength of approx. 10 to 20 mA.

German utility model DE 20 2013 104 554 U1 discloses an EMS vest in which the electrodes are attached to neoprene surface sections facing the front of the body and the back of the body by means of a hook-and-loop fastener. The surface sections are connected by strips made of a very stretchable material and facing the body flanks and by means of a large number of pull straps or lashing straps, whereby the fixation of the vest to the body of the trainee has to be carried out by means of the lashing straps, which is extensive.

U.S. Pat. No. 7,072,721 B1 also discloses an EMS vest with electrodes that can be attached by hook-and-loop fastener, but without annoying lashing straps. However, it remains silent about the construction and material of the vest.

An EMS electrode, for example, can be found in German patent application DE 10 2007 046 886 A1. EMS garments equipped with such EMS electrodes are wetted before training and usually worn over an undergarment (e.g. stretch T-shirt). For example, a set of EMS electrodes used for an EMS workout consists of electrodes attached to a vest to stimulate the trunk muscles, two electrodes attached to a bottom belt, as well as two upper arm belts and two thigh belts with EMS electrodes. In order to increase the wearing comfort of the EMS garment and optimize its fit to the body, such garments often consist of stretch fabrics with elastane fibers, wherein the EMS electrodes are also often made of textile materials with woven elastane fibers to ensure a good fit to the body. An example of such an EMS garment can be found in German patent DE 10 2009 017 179 B4.

The disadvantage of this is that such EMS garments, which consist of stretchable textiles, wear out over time.

There are also textile-integrated EMS electrodes which are integrated into the carrier textile as a whole or at least in their current transmission area, whereby not only the electrodes but also the conductor tracks connected to the electrodes are integrated into the EMS garment. German patent application DE 10 2012 112 153 A1 and international patent application WO 2014/000736A2 show textile-integrated EMS electrodes whose current transmission area is incorporated as an island inlay in a flat knitted fabric and is connected to a power connection by a connecting cable, which is also knitted in and runs in a channel.

Particularly with such textile-integrated EMS electrodes, special attention is paid to the fact that they must also have a certain elasticity, since the EMS garments and with them the EMS electrodes should fit closely to the body. The elasticity of the EMS electrodes cannot be achieved with the conductive threads used for the knitted fabrics, or only with expensive special threads that are both conductive and elastic.

Furthermore, in the field of NMES (neuromuscular stimulation) there are neoprene garments equipped with pockets in which electrodes are arranged, see US 2016/0303363 A1.

SUMMARY OF THE INVENTION

Based on this, it is an object of the present invention to create an EMS garment with improved durability and fit that is cost-effective to manufacture.

According to the invention, an EMS garment is proposed for enclosing a body part of a user during an EMS training session, which may be designed as a vest or bottom strap, for example. The EMS garment is equipped with a plurality of EMS electrodes for transmitting EMS stimuli consisting of current pulses and/or alternating current with predetermined values such as amplitude and frequency from a connected EMS stimulation generation unit to the enclosed body part. Furthermore, the EMS garment has textile area sections that lie flat against the body part during training. To ensure good contact with the body part, the EMS electrodes are designed as a pad or textile structural section with an electrically conductive conductive layer and attached to one or more of the textile area sections, so that they can flexibly snuggle to the body part.

The EMS garment according to the invention is characterized by the fact that in sections facing a front side and a rear side of the body part during training, at least one of the textile area sections is arranged on the garment, respectively, wherein the textile area sections facing the front side and the rear side are connected by stretch sections which consist of a rubber-elastic, non-textile material and preferably face the two flanks of the body part.

The stretch sections may consist of an elastomeric solid material, wherein vulcanized silicone rubber in particular has proved to be suitable with regard to the required compression on the body part to be enclosed and the elasticity and resilient restoring force required for this.

However, it would also be conceivable to form the stretch sections in the manner of a corset, each with a rubber-elastic band, which is guided by eyelets at the edge of the two textile area sections to be connected to each other, in order to provide the permanent elasticity necessary for the long-term fit of the EMS garment.

In contrast to EMS garments, where the fit or support of the body part to be trained is produced by means of stretchable textiles such as elastane or fabrics provided with elastane fibres, stretch sections consisting of rubber-elastic, non-textile materials can be used to produce much more durable EMS garments, which do not wear out so quickly under stress and also do not lose their elasticity during washing, even at high temperatures desired for hygienic reasons. In addition, such stretch sections can be produced at low cost and allow the EMS garment to be assembled at low cost overall, as adjustment straps can be omitted.

In addition, there is no need to use elastic EMS electrodes. Even if textile EMS electrodes are preferred for the inventive EMS garment due to their more pleasant wearing properties, it would also be conceivable to return to the favorable polymer pads used in earlier times as EMS electrodes, which are filled with conductive particles (e.g. soot), as can be seen for example from German patent specification DE 20 18 239 C2.

Within the scope of the invention, it would also be conceivable to provide only one stretch section made of the rubber-elastic, non-textile material on only one flank of the body, or even to relocate the stretch section to the rear side area.

It is particularly preferred if each of the stretch sections is formed as a planar extending area element. For example, a number of planar stretch strips made of rubber-elastic material can be provided along each side of the body from bottom to top in order to connect the textile area section at the back with the two front halves of an EMS vest, each of which is designed as a textile area section. However, a one-piece area element is considerably less susceptible to damage and easier to attach to the textile area sections. Therefore a stretch section formed as a one-piece area element is preferably provided on each of the two body flanks in order to connect there the rear textile area section with its edge facing the stretch section to a front textile area section with its edge facing the stretch section.

When designing the stretch sections, care must be taken to ensure that they are designed to withstand continuous tensile loads during EMS training and temperature and friction loads during washing cycles, and that they therefore have a certain basic robustness. Therefore, the stretch sections preferably have holes which provide increased stretchability with reduced elastic recovery force in the tensile direction when enclosing the body part by the EMS garment, as opposed to a stretch section without holes. Although the stretch section could simply be made thinner, this would make it more susceptible. It is also preferred if the holes have a circular or even better oval shape, with the longitudinal axis of the oval in the tensile direction, so that a particularly even force distribution can be achieved in the stretch section.

The rubber-elastic stretch sections provided for in the invention have a particularly advantageous effect if the EMS garment, which has the necessary elasticity by means of the rubber-elastic stretch sections, does not otherwise contain elastane or similar, elastically stretchable yarns or weaving or knitting techniques for the textile area sections and instead is made of an elastane-free textile material which is not elastically stretchable. This avoids the wear out of the EMS garment described above and thus not only a high degree of wear and tear, but also the usually necessary adjusting straps with which a conventional EMS garment has to be fastened to the body part to be trained, because otherwise the compression or pressing force required for effective training cannot be produced for every physique of the trainee and in every phase of wear and tear of purely textile EMS garments.

Furthermore, the EMS electrodes are also preferred with a structure without elastic stretching capability, because this avoids the costly interweaving of electrically conductive yarns with stretchable yarns or the use of expensive yarns that have both properties. It would, however, be conceivable, for example, on a bottom strap which only carries EMS electrodes on its rear textile surface section, to form front textile area sections elastically stretchable.

If each of the stretch sections consists of an elastomeric solid material such as vulcanised silicone rubber, the stretch sections can be connected to the textile area sections in a simple and stable way by sewing them together. However, it would be conceivable to bond or vulcanise the textile area sections to the stretch sections formed as elastomeric area elements.

In an advantageous further development, the textile area section facing the rear side is formed in one piece and is connected on its two sides to at least one of the stretch sections, preferably to exactly one stretch section formed in one piece as an elastomeric area element, which stretch section extends along the height direction of the erected body part which is enclosed by the EMS garment. The area of the EMS garment facing the front side of the body part can be formed by two textile area sections which are preferably of approximately equal size, i.e. which each form one half of the front side of the EMS garment and on their side facing the body flank are each connected to the at least one stretch section there. To enclose the body part with the EMS garment or to put on the EMS garment, a detachable fastener such as a zip fastener or one or more plug connections can then be provided, via which the two front textile area sections can be connected to each other. For an EMS vest, a zipper is particularly suitable for this purpose, whereby a hook strip would also be conceivable as an alternative or supplement to this. An EMS garment formed as a bottom strap, on the other hand, could be fitted with a belt-buckle or with a plug-in connection attached to the two front textile area sections with belt straps, as is known from outdoor backpacks.

Overall, there are advantages in terms of an optimum fit and an enormous durability of the EMS garment thanks to the combination of vulcanized silicone rubber and textile area sections, as well as an ideal force-elongation behavior with high elasticity due to the stretch sections consisting of vulcanized silicone rubber. High elastic restoring forces ensure an ideal contact pressure of the electrodes and the necessary compression of the EMS garment onto the body part to be enclosed, without material fatigue or wear out of the EMS garment during continuous use. Silicone rubber has long been used in medical applications and is also suitable for use on EMS garment or clothing due to its antibacterial properties. In addition, there is an enormous anti-slip effect which prevents the EMS garment from slipping during training.

BRIEF DESCRIPTION OF THE DRAWINGS

In the following, advantageous embodiments of the invention are described in more detail on the basis of the enclosed drawings.

DETAILED DESCRIPTION OF THE PREFERRED EMBODIMENTS

Figure 1:
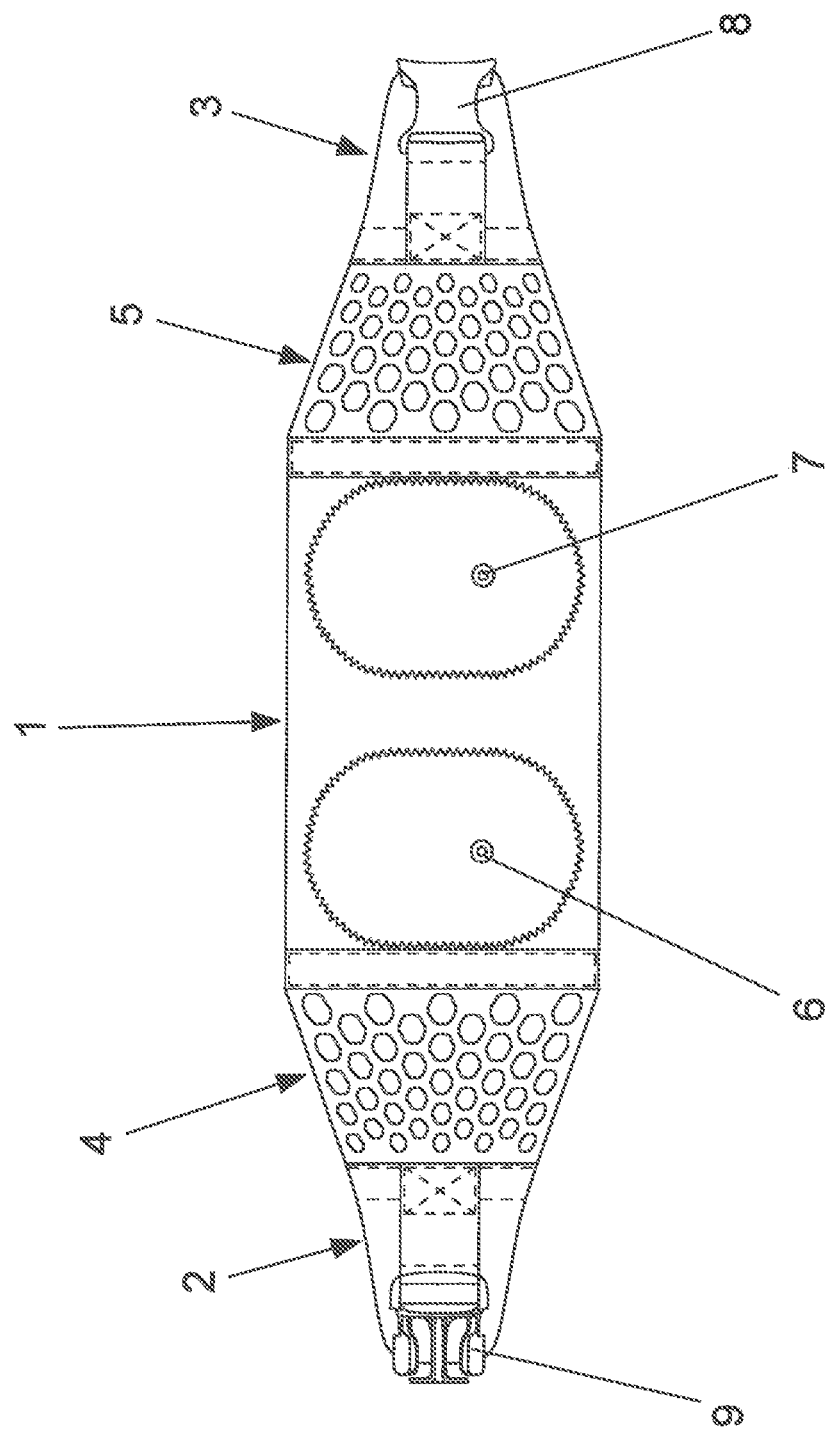
FIG. 1 shows a bottom strap according to an advantageous embodiment of the invention.

First, reference is made to FIG. 1, which shows an EMS garment formed as a bottom or butt strap. The EMS bottom strap or belt has a textile area section 1 on its area facing the back of the body when in the applied state, which has two EMS electrodes assigned to the two buttocks, the push buttons of which are marked 6, 7 for connecting power connection cables. At its two side edges, the rear textile area section 1 is sewn to a flat, one-piece stretch section 4, 5 made of vulcanized silicone rubber. Each of the two stretch sections 4, 5 can have circular holes in order to be able to select the thickness of the stretch section 4, 5 so high that, despite the desired stretchability, the stretch sections 4, 5 have a high robustness. At their front edge area facing away from the rear textile area section 1, the two stretch sections 4, 5 are each connected, preferably sewn, to a further textile area section 2, 3. The two textile area sections 2, 3 each carry belt straps with plug-in elements 8, 9, with which they can be connected to each other on the front side of the body after putting on the bottom strap. The textile area sections 1, 2, 3 do not need to have any elasticity, so that the elasticity required for the precise fitting of the bottom strap to the body is provided solely by the two stretching sections 4, 5.

Figure 2:
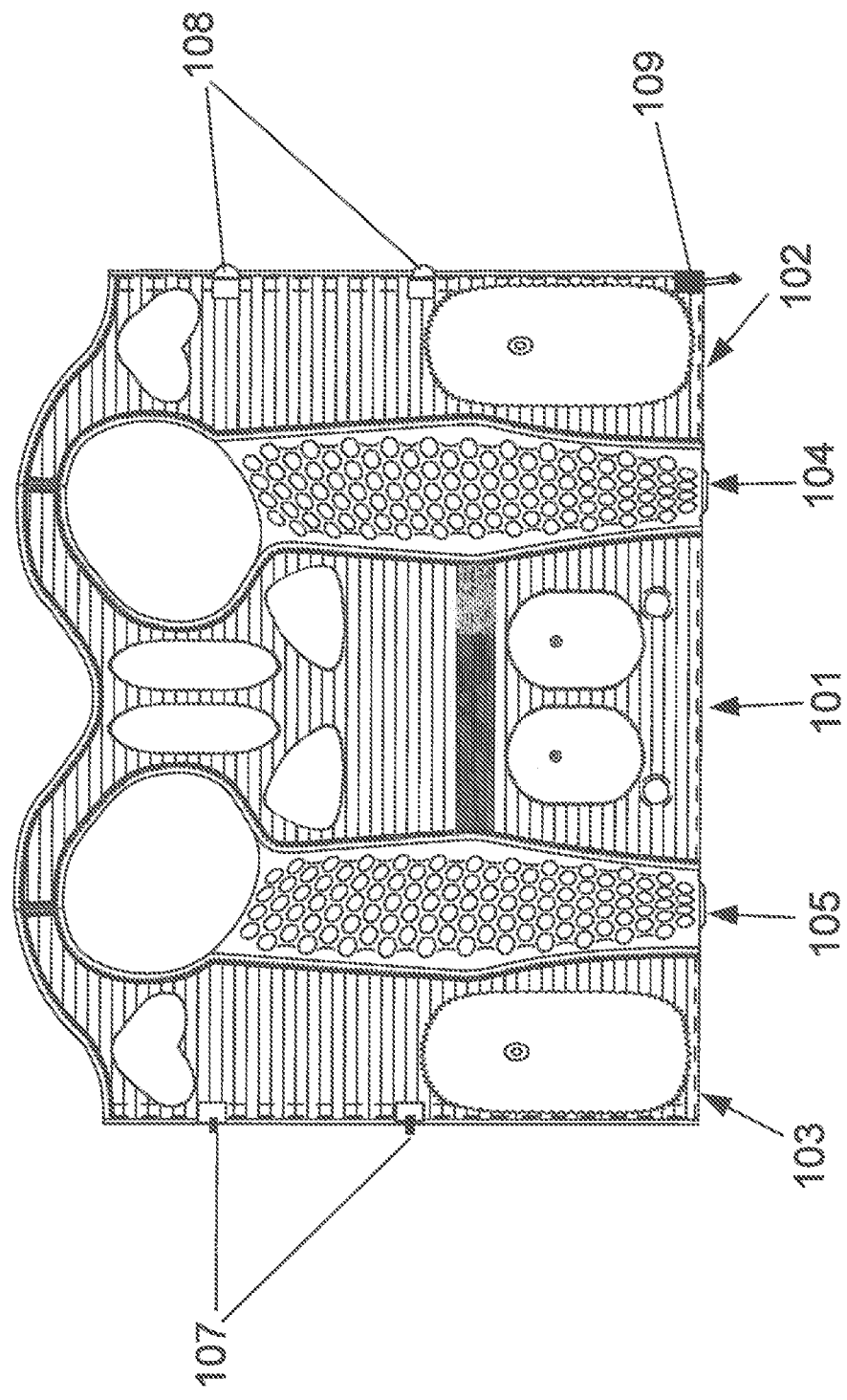
FIG. 2 shows an EMS vest according to a further advantageous embodiment of the invention.
Figure 3:
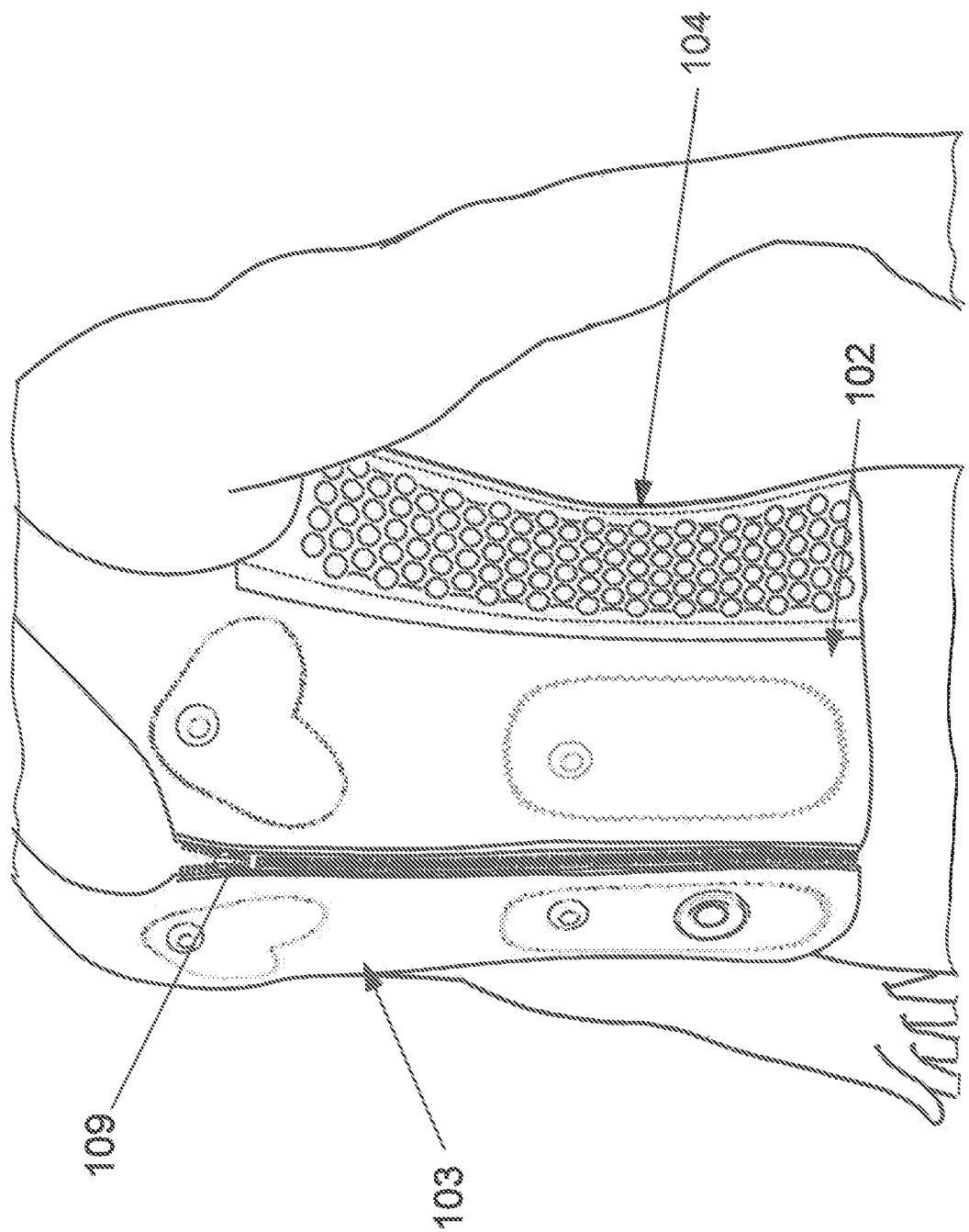
FIG. 3 the EMS vest shown in FIG. 2 in a state wherein it is applied to a mannequin.

FIGS. 2 and 3 show an EMS garment formed as a vest with three pairs of electrodes on the back of the body and two pairs of electrodes on the front. A one-piece textile area section facing the back part of the trainee having the three pairs of electrodes is designated 101 and sewn above the arm loops with two further textile area sections 102, 103 each with two EMS electrodes provided for contact with the front of the body. Below the two arm loops, two one-piece stretch sections 104, 105, consisting of vulcanized silicone rubber, extend along the height direction of the erected body and are connected, preferably sewn, along their side edges to the facing side edges of the respective textile area sections 101, 102 or 101, 103. The elastic restoring force or compression of the vest required for a planar contact of the EMS electrodes to the torso of the trainee is provided solely by the two elastomer stretch sections 104, 105, if a zipper 109 running in the direction of the upright body is closed on the belly side. Furthermore, the EMS vest has hooks 107 on the one hand and eyelets 108 on the other, on which the two front textile area sections 102, 103 can be pre-fixed to each other before closing the zipper 109.

Variations and modifications are possible without leaving the scope of the invention.

For example, upper arm or thigh straps could also be provided with corresponding, preferably one-piece, elastomeric stretch sections, which would make the adjustment loops and Velcro fasteners previously required for lashing obsolete.

The invention claimed is:

1. An EMS garment, forming a vest for enclosing a body part of a trainee during an EMS training session, comprising textile area sections for plane snuggeling to the body part, and EMS electrodes for transmitting EMS stimuli consisting of current pulses and/or alternating current with predetermined values such as amplitude and frequency from a connected EMS stimulation generating unit to the body part, which EMS electrodes are each connected to one of the textile area sections and are each formed as a pad or a textile structure section having an electrically conductive layer so as to flexibly snuggle to the body part, wherein the EMS garment comprises, in regions facing the front side and the rear side of the body part, at least one of the textile area sections, wherein the textile area sections facing the front side and the rear side are connected along a height direction of the erected body part by stretch sections facing both flanks of the body part, each of which consists of a rubber-elastic, elastomeric solid material, wherein:

a flexibility of the stretch sections is greater than a flexibility of the textile area sections, the textile area section facing the rear side is formed in one piece and is connected on each of its two sides to at least one of the stretch sections, and the region of the EMS garment facing the front side being formed by two textile area sections of approximately equal size, which on their side facing the respective body flank are each connected to the at least one stretch portion there and which are connectable to one another for enclosing the body part with the EMS garment via a detachable closure such as a zipper or a plug-in connection.

2. EMS garment according to claim 1, wherein the stretch sections are each designed as a planarly extending flat element.

3. EMS garment according to claim 2, wherein the stretch sections are each provided with holes.

4. EMS garment according to claim 3, wherein the holes are circular or oval.

5. EMS garment according to claim 1, wherein on each of the two body flanks, only one of the stretch sections is provided and being formed in one piece.

6. An EMS garment according to claim 5, wherein the elastomeric solid material of which the stretch sections consist is a vulcanized silicone rubber.

7. An EMS garment according to claim 1, wherein the elastomeric solid material of which the stretch sections consist is a vulcanized silicone rubber.

8. An EMS garment according to claim 7, wherein the stretch portions are sewn to the textile area sections.

9. EMS garment according to claim 7, wherein the textile area section facing the rear side, and also the textile area sections on the front side, carry EMS electrodes.

10. EMS garment according to claim 7, wherein the EMS electrodes have a structure not being elastically stretchable.

11. EMS garment according to claim 10, wherein at least each textile area section carrying EMS electrodes consists of an elastane-free textile material not being non elastically stretchable.

12. EMS garment according to claim 1, wherein the textile area section facing the rear side, and also the textile area sections on the front side, carry EMS electrodes.

* * * * *